(12) United States Patent
Stürmer et al.

(10) Patent No.: US 8,313,923 B2
(45) Date of Patent: Nov. 20, 2012

(54) PROCESS FOR ENZYMATIC REDUCTION OF ALKENE DERIVATIVES

(75) Inventors: Rainer Stürmer, Rödersheim-Gronau (DE); Bernhard Hauer, Fussgönheim (DE); Thomas Friedrich, Darmstadt (DE); Kurt Faber, Graz (AT); Melanie Hall, Plouarzel (FR)

(73) Assignee: BASF SE, Ludwigshafen (DE)

( * ) Notice: Subject to any disclaimer, the term of this patent is extended or adjusted under 35 U.S.C. 154(b) by 440 days.

(21) Appl. No.: 12/514,215

(22) PCT Filed: Nov. 13, 2007

(86) PCT No.: PCT/EP2007/062251

§ 371 (c)(1),
(2), (4) Date: May 8, 2009

(87) PCT Pub. No.: WO2008/058951

PCT Pub. Date: May 22, 2008

(65) Prior Publication Data

US 2010/0035315 A1   Feb. 11, 2010

(30) Foreign Application Priority Data

Nov. 15, 2006 (EP) .................................. 06124126
Dec. 22, 2006 (EP) .................................. 06126993

(51) Int. Cl.
*C12P 7/26* (2006.01)

(52) U.S. Cl. ........................... 435/61; 435/7.1; 530/350
(58) Field of Classification Search .................. None
See application file for complete search history.

(56) References Cited

U.S. PATENT DOCUMENTS 6,596,520 B1 * 7/2003 Friedrich et al. .............. 435/135

FOREIGN PATENT DOCUMENTS

| DE | 10019377 A1 | 10/2001 |
|---|---|---|
| EP | 1069183 A3 | 7/2002 |
| EP | 1149849 B1 | 5/2003 |
| EP | 1473368 A1 | 11/2004 |
| JP | 2002023395 A | 1/2002 |
| JP | 2002-233395 A | 8/2002 |
| JP | 2005027552 A | 2/2005 |
| JP | 2006174726 A | 7/2006 |

OTHER PUBLICATIONS

Strassner, et al., "A Homolog of Old Yellow Enzyme in Tomato", The Journal of Biological Chemistry, vol. 274, No. 49, pp. 35067-35073, Dec. 3, 1999.

Fitzpatrick, et al., "Characterization of YqjM, an Old Yellow Enzyme Homolog from *Bacillus subtilis* Involved in the Oxidative Stress Response", The Journal of Biological Chemistry, vol. 278, No. 22, pp. 19891-19897, May 30, 2003.

Steinbacher, et al., "Enoate Reductase Family", Flavins and Flavoproteins 2002, Proceedings of the Fourteenth International Symposium St. John's College, University of Cambridge, UK, Jul. 14-18, 2002, pp. 941-949, Editors: Stephen Chapman, Richard Perham, Nigel Scrutton; Agency for Scientific Publications, Rudolf Weber, Berlin 2002.

Simon, et al., "Chiral Compound Synthesized by Biocatalytic Reductions", Angew. Chem. Int. Ed. Engl., vol. 24, 1985, pp. 539-553.

Hall, et al., "Asymmetric whole-cell bioreduction of an α,β-unsaturated aldehyde (citral): competing *prim*-alcohol dehydrogenase and C-C lyase activities", Tetrahedron: Asymmetry, vol. 17, 2006, pp. 3058-3062.

Williams, et al., "New uses for an Old Enzyme—the Old Yellow Enzyme family of flavoenzymes", Microbiology, 2002, vol. 148, pp. 1607-1614.

Lalonde, et al., "Immobilization of Enzymes", Enzyme Catalysis in Organic Synthesis, A Comprehensive Handbook, vol. I, edited by Karlheinz Drauz and Herbert Waldmann, Second Ed., pp. 163-184.

* cited by examiner

*Primary Examiner* — Hope Robinson
(74) *Attorney, Agent, or Firm* — Connolly Bove Lodge & Hutz LLP

(57) ABSTRACT

A method for enzymatic preparation of compounds of the general formula (2) from unsaturated alkene derivatives of the general formula (1) by reducing a compound of the formula (1) in the presence of a reductase, comprising at least one of the polypeptide sequences SEQ ID NO: 1, 2 or 3 or having a functionally equivalent polypeptide sequence which is at least 80% identical to SEQ ID NO: 1, 2 or 3.

10 Claims, No Drawings

SEQUENCE LISTING

```
<160> NUMBER OF SEQ ID NOS: 3

<210> SEQ ID NO 1
<211> LENGTH: 337
<212> TYPE: PRT
<213> ORGANISM: Bacillus subtilis

<400> SEQUENCE: 1

Ala Arg Lys Leu Phe Thr Pro Ile Thr Ile Lys Asp Met Thr Leu Lys
1               5                   10                  15

Asn Arg Ile Val Met Ser Pro Met Cys Met Tyr Ser Ser His Glu Lys
            20                  25                  30

Asp Gly Lys Leu Thr Pro Phe His Met Ala His Tyr Ile Ser Arg Ala
        35                  40                  45

Ile Gly Gln Val Gly Leu Ile Ile Val Glu Ala Ser Ala Val Asn Pro
    50                  55                  60

Gln Gly Arg Ile Thr Asp Gln Asp Leu Gly Ile Trp Ser Asp Glu His
65                  70                  75                  80

Ile Glu Gly Phe Ala Lys Leu Thr Glu Gln Val Lys Glu Gln Gly Ser
                85                  90                  95

Lys Ile Gly Ile Gln Leu Ala His Ala Gly Arg Lys Ala Glu Leu Glu
```

-continued

```
                100                 105                 110
Gly Asp Ile Phe Ala Pro Ser Ala Ile Ala Phe Asp Glu Gln Ser Ala
            115                 120                 125

Thr Pro Val Glu Met Ser Ala Glu Lys Val Lys Glu Thr Val Gln Glu
130                 135                 140

Phe Lys Gln Ala Ala Arg Ala Lys Glu Ala Gly Phe Asp Val Ile
145                 150                 155                 160

Glu Ile His Ala Ala His Gly Tyr Leu Ile His Glu Phe Leu Ser Pro
                165                 170                 175

Leu Ser Asn His Arg Thr Asp Glu Tyr Gly Gly Ser Pro Glu Asn Arg
            180                 185                 190

Tyr Arg Phe Leu Arg Glu Ile Ile Asp Glu Val Lys Gln Val Trp Asp
        195                 200                 205

Gly Pro Leu Phe Val Arg Val Ser Ala Ser Asp Tyr Thr Asp Lys Gly
    210                 215                 220

Leu Asp Ile Ala Asp His Ile Gly Phe Ala Lys Trp Met Lys Glu Gln
225                 230                 235                 240

Gly Val Asp Leu Ile Asp Cys Ser Ser Gly Ala Leu Val His Ala Asp
                245                 250                 255

Ile Asn Val Phe Pro Gly Tyr Gln Val Ser Phe Ala Glu Lys Ile Arg
            260                 265                 270

Glu Gln Ala Asp Met Ala Thr Gly Ala Val Gly Met Ile Thr Asp Gly
        275                 280                 285

Ser Met Ala Glu Glu Ile Leu Gln Asn Gly Arg Ala Asp Leu Ile Phe
    290                 295                 300

Ile Gly Arg Glu Leu Leu Arg Asp Pro Phe Phe Ala Arg Thr Ala Ala
305                 310                 315                 320

Lys Gln Leu Asn Thr Glu Ile Pro Ala Pro Val Gln Tyr Glu Arg Gly
                325                 330                 335

Trp

<210> SEQ ID NO 2
<211> LENGTH: 376
<212> TYPE: PRT
<213> ORGANISM: Lycopersicon esculentum

<400> SEQUENCE: 2

Met Glu Asn Lys Val Val Glu Glu Lys Gln Val Asp Lys Ile Pro Leu
1               5                   10                  15

Met Ser Pro Cys Lys Met Gly Lys Phe Glu Leu Cys His Arg Val Val
            20                  25                  30

Leu Ala Pro Leu Thr Arg Gln Arg Ser Tyr Gly Tyr Ile Pro Gln Pro
        35                  40                  45

His Ala Ile Leu His Tyr Ser Gln Arg Ser Thr Asn Gly Gly Leu Leu
    50                  55                  60

Ile Gly Glu Ala Thr Val Ile Ser Glu Thr Gly Ile Gly Tyr Lys Asp
65                  70                  75                  80

Val Pro Gly Ile Trp Thr Lys Glu Gln Val Glu Ala Trp Lys Pro Ile
                85                  90                  95

Val Asp Ala Val His Ala Lys Gly Gly Ile Phe Phe Cys Gln Ile Trp
            100                 105                 110

His Val Gly Arg Val Ser Asn Lys Asp Phe Gln Pro Asn Gly Glu Asp
        115                 120                 125

Pro Ile Ser Cys Thr Asp Arg Gly Leu Thr Pro Gln Ile Arg Ser Asn
    130                 135                 140
```

```
Gly Ile Asp Ile Ala His Phe Thr Arg Pro Arg Arg Leu Thr Thr Asp
145                 150                 155                 160

Glu Ile Pro Gln Ile Val Asn Glu Phe Arg Val Ala Ala Arg Asn Ala
                165                 170                 175

Ile Glu Ala Gly Phe Asp Gly Val Glu Ile His Gly Ala His Gly Tyr
            180                 185                 190

Leu Ile Asp Gln Phe Met Lys Asp Gln Val Asn Asp Arg Ser Asp Lys
        195                 200                 205

Tyr Gly Gly Ser Leu Glu Asn Arg Cys Arg Phe Ala Leu Glu Ile Val
    210                 215                 220

Glu Ala Val Ala Asn Glu Ile Gly Ser Asp Arg Val Gly Ile Arg Ile
225                 230                 235                 240

Ser Pro Phe Ala His Tyr Asn Glu Ala Gly Asp Thr Asn Pro Thr Ala
                245                 250                 255

Leu Gly Leu Tyr Met Val Glu Ser Leu Asn Lys Tyr Asp Leu Ala Tyr
            260                 265                 270

Cys His Val Val Glu Pro Arg Met Lys Thr Ala Trp Glu Lys Ile Glu
        275                 280                 285

Cys Thr Glu Ser Leu Val Pro Met Arg Lys Ala Lys Gly Thr Phe
    290                 295                 300

Ile Val Ala Gly Gly Tyr Asp Arg Glu Asp Gly Asn Arg Ala Leu Ile
305                 310                 315                 320

Glu Asp Arg Ala Asp Leu Val Ala Tyr Gly Arg Leu Phe Ile Ser Asn
                325                 330                 335

Pro Asp Leu Pro Lys Arg Phe Glu Leu Asn Ala Pro Leu Asn Lys Tyr
            340                 345                 350

Asn Arg Asp Thr Phe Tyr Thr Ser Asp Pro Ile Val Gly Tyr Thr Asp
        355                 360                 365

Tyr Pro Phe Leu Glu Thr Met Thr
    370                 375

<210> SEQ ID NO 3
<211> LENGTH: 396
<212> TYPE: PRT
<213> ORGANISM: Lycopersicon esculentum

<400> SEQUENCE: 3

Met Ala Ser Ser Ala Gln Asp Gly Asn Asn Pro Leu Phe Ser Pro Tyr
1               5                   10                  15

Lys Met Gly Lys Phe Asn Leu Ser His Arg Val Val Leu Ala Pro Met
                20                  25                  30

Thr Arg Cys Arg Ala Leu Asn Asn Ile Pro Gln Ala Ala Leu Gly Glu
            35                  40                  45

Tyr Tyr Glu Gln Arg Ala Thr Ala Gly Gly Phe Leu Ile Thr Glu Gly
        50                  55                  60

Thr Met Ile Ser Pro Thr Ser Ala Gly Phe Pro His Val Pro Gly Ile
65                  70                  75                  80

Phe Thr Lys Glu Gln Val Arg Glu Trp Lys Lys Ile Val Asp Val Val
                85                  90                  95

His Ala Lys Gly Ala Val Ile Phe Cys Gln Leu Trp His Val Gly Arg
            100                 105                 110

Ala Ser His Glu Val Tyr Gln Pro Ala Gly Ala Ala Pro Ile Ser Ser
        115                 120                 125

Thr Glu Lys Pro Ile Ser Asn Arg Trp Arg Ile Leu Met Pro Asp Gly
    130                 135                 140
```

```
Thr His Gly Ile Tyr Pro Lys Pro Arg Ala Ile Gly Thr Tyr Glu Ile
145                 150                 155                 160

Ser Gln Val Val Glu Asp Tyr Arg Arg Ser Ala Leu Asn Ala Ile Glu
                165                 170                 175

Ala Gly Phe Asp Gly Ile Glu Ile His Gly Ala His Gly Tyr Leu Ile
            180                 185                 190

Asp Gln Phe Leu Lys Asp Gly Ile Asn Asp Arg Thr Asp Glu Tyr Gly
        195                 200                 205

Gly Ser Leu Ala Asn Arg Cys Lys Phe Ile Thr Gln Val Val Gln Ala
                210             215                 220

Val Val Ser Ala Ile Gly Ala Asp Arg Val Gly Val Arg Val Ser Pro
225                 230                 235                 240

Ala Ile Asp His Leu Asp Ala Met Asp Ser Asn Pro Leu Ser Leu Gly
                245                 250                 255

Leu Ala Val Val Glu Arg Leu Asn Lys Ile Gln Leu His Ser Gly Ser
                260                 265                 270

Lys Leu Ala Tyr Leu His Val Thr Gln Pro Arg Tyr Val Ala Tyr Gly
            275                 280                 285

Gln Thr Glu Ala Gly Arg Leu Gly Ser Glu Glu Glu Ala Arg Leu
    290                 295                 300

Met Arg Thr Leu Arg Asn Ala Tyr Gln Gly Thr Phe Ile Cys Ser Gly
305                 310                 315                 320

Gly Tyr Thr Arg Glu Leu Gly Ile Glu Ala Val Ala Gln Gly Asp Ala
                325                 330                 335

Asp Leu Val Ser Tyr Gly Arg Leu Phe Ile Ser Asn Pro Asp Leu Val
            340                 345                 350

Met Arg Ile Lys Leu Asn Ala Pro Leu Asn Lys Tyr Asn Arg Lys Thr
            355                 360                 365

Phe Tyr Thr Gln Asp Pro Val Val Gly Tyr Thr Asp Tyr Pro Phe Leu
    370                 375                 380

Gln Gly Asn Gly Ser Asn Gly Pro Leu Ser Arg Leu
385                 390                 395
```

PROCESS FOR ENZYMATIC REDUCTION OF ALKENE DERIVATIVES

RELATED APPLICATIONS

This application is a national stage application (under 35 U.S.C. §371) of PCT/EP2007/062251, filed Nov. 13, 2007, which claims benefit of European Application No. 06124126.1, filed Nov. 15, 2006, and European Application No. 06126993.2, filed Dec. 22, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_12810_00891_US. The size of the text file is 10 KB, and the text file was created on May 8, 2009.

The invention relates to a process for the enzymatic reduction of alkene derivatives of the general formula (1).

OBJECT OF THE INVENTION

It was the object to provide a process for enzymatic preparation of compounds of the general formula (2) from unsaturated alkene derivatives of the general formula (1), in particular with high chemical yield and very good stereoselectivity.

SUMMARY OF THE INVENTION

The above object was solved by using the reductases YqjM, OPR1, OPR3 and functional equivalents thereof for reducing alkene derivatives of the general formula (1).

DETAILED DESCRIPTION OF THE INVENTION

The present invention relates to a process for enzymatic preparation of compounds of the general formula (2) from unsaturated alkene derivatives of the general formula (1)

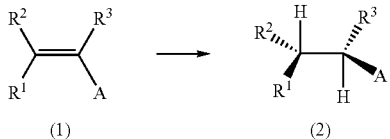

in which

A is a nitro radical (—$NO_2$), a ketone radical (—CRO), an aldehyde radical (—CHO), a carboxyl radical (—COOR), with R=H or optionally substituted $C_1$-$C_6$-alkyl radical, $R^1$, $R^2$ and $R^3$ are independently of one another H, $C_1$-$C_6$-alkyl, $C_2$-$C_6$-alkenyl, carboxyl, or an optionally substituted carbo- or heterocyclic, aromatic or nonaromatic radical, or $R^1$ is linked to $R^3$ so as to become part of a 4-8-membered cycle, or $R^1$ is linked to R so as to become part of a 4-8-membered cycle, with the proviso that $R^1$, $R^2$ and $R^3$ may not be identical, by reducing a compound of the formula (1) in the presence of a reductase
(i) comprising at least one of the polypeptide sequences SEQ ID NO: 1, 2, or 3 or
(ii) with a functionally equivalent polypeptide sequence which is at least 80% identical to SEQ ID NO: 1, 2, or 3.

In principle, the process of the invention can be carried out both with purified or concentrated enzyme itself and with microorganisms which express this enzyme naturally or recombinantly, or with cell homogenates derived therefrom.

Unless stated otherwise, $C_1$-$C_6$-alkyl means in particular methyl, ethyl, propyl, butyl, pentyl or hexyl and the corresponding singly or multiply branched analogs such as isopropyl, isobutyl, sec-butyl, tert-butyl, isopentyl or neopentyl; with preference being given in particular to the $C_1$-$C_4$-alkyl radicals;

$C_2$-$C_6$-alkenyl means in particular the monounsaturated analogs of the above-mentioned alkyl radicals having from 2 to 6 carbon atoms, with preference being given in particular to the corresponding $C_2$-$C_4$-alkenyl radicals, carboxyl means in particular the group COOH, carbo- and heterocyclic aromatic or nonaromatic rings mean in particular optionally fused rings having from 3 to 12 carbon atoms and if appropriate from 1 to 4 heteroatoms such as N, S and O, in particular N or O. Examples which may be mentioned are cyclopropyl, cyclobutyl, cyclopentyl, cyclohexyl, cycloheptyl, the mono- or polyunsaturated analogs thereof such as cyclobutenyl, cyclopentenyl, cyclohexenyl, cycloheptenyl, cyclohexadienyl, cycloheptadienyl; phenyl and naphthyl; and 5- to 7-membered saturated or unsaturated heterocyclic radicals having from 1 to 4 heteroatoms which are selected from O, N and S, where the heterocycle may optionally be fused to a further heterocycle or carbocycle. Mention should be made in particular of heterocyclic radicals derived from pyrrolidine, tetrahydrofuran, piperidine, morpholine, pyrrole, furan, thiophene, pyrazole, imidazole, oxazole, thiazole, pyridine, pyran, pyrimidine, pyridazine, pyrazine, coumarone, indole and quinoline. The cyclic radicals, but also the abovementioned alkyl and alkenyl radicals, may optionally be substituted one or more times, such as, for example, 1, 2 or 3 times. Mention should be made as examples of suitable substituents of: halogen, in particular F, Cl, Br; —OH, —SH, —$NO_2$, —$NH_3$, —$SO_3H$, $C_1$-$C_4$-alkyl and $C_2$-$C_4$-alkenyl, $C_1$-$C_4$-alkoxy; and hydroxy-$C_1$-$C_4$-alkyl; where the alkyl and alkenyl radicals are as defined above, and the alkoxy radicals are derived from the above-defined corresponding alkyl radicals.

The radicals $R^1$ and $R^3$ may also be linked directly to one another so as to form together with the double bond to be reduced a 4-8-, preferably a 5- or 6-membered cycle, for example a cyclopentene or cyclohexene structure which may also be optionally substituted, for example by alkyl, preferably methyl radicals.

The radicals $R^1$ and R may also be linked directly to one another so as to form together with the double bond to be reduced a 4-8-, preferably a 5- or 6-membered cycle, for example a cyclopentene or cyclohexene structure which may also be optionally substituted, for example by alkyl, preferably methyl radicals.

The abovementioned 4-8-membered cycles may be both carbocycles, i.e. only carbon atoms form the cycle, and heterocycles, i.e. heteroatoms such as O; S; N, are present in the cycle. If desired, these carbo- or heterocycles may also still be substituted, i.e. hydrogen atoms are replaced with heteroatoms. For example, N-phenylsuccinimides (see substrate 3 below) are to be considered such substituted heterocycles which are the result of $R^1$ and R forming a cycle.

Particularly advantageous embodiments of the invention comprise the enzymatic reduction of the following substrates (compounds of the general formula 1) to the corresponding compounds of the general formula (2):

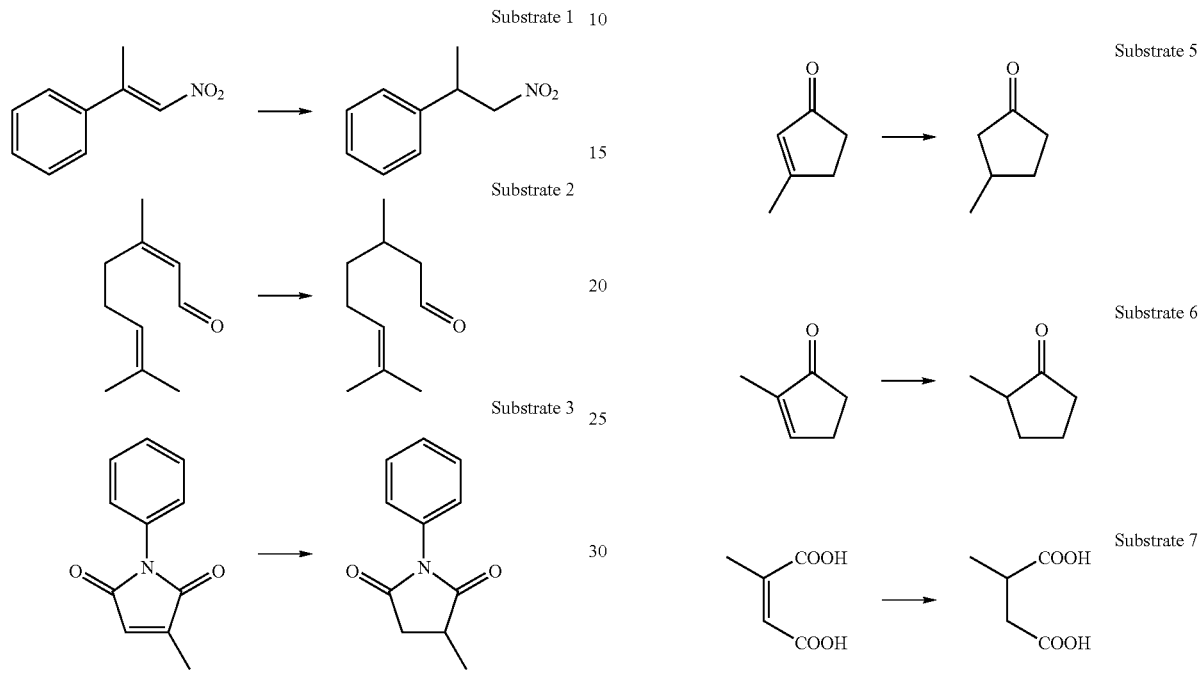

TABLE 1

| | | OPR1 | | OPR3 wt | | YqjM | |
|---|---|---|---|---|---|---|---|
| Substrate | Cofactor | % | E.e. % | % | E.e. % | % | E.e. % |
| 1 | NADH | >99 | (R) 97 | 69 | (S) 82 | 94 | (S) 92 |
| 1 | NADPH | >99 | (R) 96 | 72 | (S) 87 | 85 | (S) 70 |
| 1 | NAD$^+$-FDH | >90 | (R) 95 | 40 | (S) 75 | 50 | (S) 85 |
| 1 | NADP$^+$-G6PDH | 90 | (R) 98 | 75 | (S) 93 | 47 | (S) 84 |
| 2 | NADH | >99 | (S) >95 | 90 | (S) >95 | 70 | (S) >95 |
| 2 | NADPH | >99 | (S) >95 | 90 | (S) >95 | 73 | (S) >95 |
| 2 | NAD$^+$-FDH | Main product: Citronellol (saturated alcohol) | | | | | |
| 2 | NAD$^+$-GDH | 20 | (S) >95 | 90 | (S) >95 | 3 | (S) >95 |
| 2 | NADP$^+$-G6PDH | 15 | (S) >95 | 95 | (S) >95 | 57 | (S) >95 |
| 3 | NADH | 58 | (S) 61 | 27 | (S) 45 | 50 | (S) 55 |
| 3 | NADPH | 45 | (S) 64 | 19 | (S) 45 | 100 | (S) 66 |
| 3 | NAD$^+$-FDH | 88 | (R) 1 | 65 | (R) 1 | 100 | (R) 2 |
| 3 | NADP$^+$-G6PDH | 14 | (S) 61 | 10 | (S) 58 | 72 | (S) 94 |
| 4 | NADH | n.c. | — | 1 | (S) >99 | 0.5 | (S) 59 |
| 4 | NADPH | n.c. | — | 2 | (S) >99 | n.c. | — |
| 4 | NAD$^+$-FDH | — | — | 5 | (S) >99 | 1 | (S) 64 |
| 4 | NADP$^+$-G6PDH | — | — | 1 | (S) >99 | — | — |
| 5 | NADH | n.c. | — | 3 | (S) >99 | n.c. | — |
| 5 | NADPH | n.c. | — | 2 | (S) >99 | n.c. | — |
| 5 | NAD$^+$-FDH | — | — | 11 | (S) >99 | — | — |
| 5 | NADP$^+$-G6PDH | — | — | 1 | (S) >99 | — | — |
| 6 | NADH | 99 | (R) >99 | 99 | (R) >99 | 99.5 | (R) >99 |
| 6 | NADPH | 99 | (R) >99 | 99 | (R) >99 | 98.5 | (R) >99 |
| 6 | NAD$^+$-FDH | 99 | (R) 97 | 99 | (R) 92 | 99 | (R) 92 |
| 6 | NADP$^+$-G6PDH | 99 | (R) 96 | 99 | (R) 97 | 99 | (R) 96 |
| 7 | NADH | >99 | (R) >99 | n.c. | — | | |
| 7 | NADPH | >99 | (R) >99 | n.c. | — | | |
| 7 | NAD$^+$-FDH | 2 | (R) >99 | n.d. | — | | |
| 7 | NADP$^+$-G6PDH | 96 | (R) >99 | n.d. | — | | |

The process of the invention may be carried out in particular with compounds of the general formula (1) in which A is an aldehyde or ketone radical and $R^1$ or $R^2$ is methyl.

The reductases suitable for the process of the invention (which are sometimes also referred to as enoate reductases) have a polypeptide sequence as set forth in SEQ ID NO: 1, 2, or 3 or a polypeptide sequence which is at least 80%, for example at least 90%, or at least 95% and in particular at least 97%, 98% or 99% identical to SEQ ID NO: 1, 2 or 3.

A polypeptide having SEQ ID NO: 1 is known under the name YqjM from *Bacillus subtilis* (UniprotKB/Swissprot entry P54550).

A polypeptide having SEQ ID NO: 2 is encoded by the tomato OPR1 gene (UniprotKB/Swissprot entry Q9XG54).

A polypeptide having SEQ ID NO: 3 is encoded by the tomato OYPR3 gene (UniprotKB/Swissprot entry Q9FEW9).

The sequence identity is to be determined for the purposes described herein by the "GAP" computer program of the Genetics Computer Group (GCG) of the University of Wisconsin, and version 10.3 using the standard parameters recommended by GCG is to be employed.

Such reductases can be obtained starting from SEQ ID NO: 1, 2, or 3 by targeted or randomized mutagenesis methods known to the skilled worker. An alternative possibility is, however, also to search in microorganisms, preferably in those of the genera *Alishewanella, Alterococcus, Aquamonas, Aranicola, Arsenophonus, Azotivirga, Brenneria, Buchnera* (aphid P-endosymbionts), *Budvicia, Buttiauxelia, Candidatus Phlomobacter, Cedecea, Cifrobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia* or *Yokenella*, for reductases which catalyze the abovementioned model reaction and whose amino acid sequence already has the required sequence identity to SEQ ID NO: 1, 2 or 3 or is obtained by mutagenesis methods.

The reductase can be used in purified or partly purified form or else in the form of the microorganism itself. Methods for obtaining and purifying dehydrogenases from microorganisms are well known to the skilled worker.

The enantioselective reduction with the reductase preferably takes place in the presence of a suitable cofactor (also referred to as cosubstrate). Cofactors normally used for reduction of the ketone are NADH and/or NADPH. Reductases can moreover be employed as cellular systems which inherently comprise cofactor, or alternative redox mediators can be added (A. Schmidt, F. Hollmann and B. BOhier "Oxidation of Alcohols" in K. Drauz and H. Waldmann, Enzyme Catalysis in Organic Synthesis 2002, Vol. III, 991-1032, Wiley-VCH, Weinheim).

The enantioselective reduction with the reductase additionally preferably takes place in the presence of a suitable reducing agent which regenerates cofactor oxidized during the reduction. Examples of suitable reducing agents are sugars, in particular hexoses such as glucose, mannose, fructose, and/or oxidizable alcohols, especially ethanol, propanol or isopropanol, and formate, phosphite or molecular hydrogen. To oxidize the reducing agent and, associated therewith, to regenerate the coenzyme it is possible to add a second dehydrogenase such as, for example, glucose dehydrogenase when glucose is used as reducing agent, or formate dehydrogenase when formate is used as reducing agent. This can be employed as free or immobilized enzyme or in the form of free or immobilized cells. Preparation thereof can take place either separately or by coexpression in a (recombinant) reductase strain.

A preferred embodiment of the claimed process is to regenerate the cofactors by an enzymatic system in which a second dehydrogenase, particularly preferably a glucose dehydrogenase, is used.

It may further be expedient to add further additions promoting the reduction, such as, for example, metal salts or chelating agents such as, for example, EDTA.

The reductases used according to the invention can be employed free or immobilized. An immobilized enzyme means an enzyme which is fixed to an inert carrier. Suitable carrier materials and the enzymes immobilized thereon are disclosed in EP-A-1149849, EP-A-1 069 183 and DE-A 100193773, and in the references cited therein. The disclosure of these publications in this regard is incorporated in its entirety herein by reference. Suitable carrier materials include for example clays, clay minerals such as kaolinite, diatomaceous earth, perlite, silicon dioxide, aluminum oxide, sodium carbonate, calcium carbonate, cellulose powder, anion exchanger materials, synthetic polymers such as polystyrene, acrylic resins, phenol-formaldehyde resins, polyurethanes and polyolefins such as polyethylene and polypropylene. The carrier materials are normally employed in a finely divided particulate form to prepare the carrier-bound enzymes, with preference for porous forms. The particle size of the carrier material is normally not more than 5 mm, in particular not more than 2 mm (grading curve). It is possible analogously to choose a free or immobilized form on use of the dehydrogenase as whole-cell catalyst. Examples of carrier materials are Ca alginate and carrageenan. Both enzymes and cells can also be crosslinked directly with glutaraldehyde (crosslinking to give CLEAs). Corresponding and further immobilization methods are described for example in J. Lalonde and A. Margolin "Immobilization of Enzymes" in K. Drauz and H. Waidmann, Enzyme Catalysis in Organic Synthesis 2002, Vol. III, 991-1032, Wiley-VCH, Weinheim.

The reaction can be carried out in aqueous or nonaqueous reaction media or in 2-phase systems or (micro)emulsions. The aqueous reaction media are preferably buffered solutions which ordinarily have a pH of from 4 to 8, preferably from 5 to 8. The aqueous solvent may, besides water, additionally comprise at least one alcohol, e.g. ethanol or isopropanol, or dimethyl sulfoxide.

Nonaqueous reaction media mean reaction media which comprise less than 1% by weight, preferably less than 0.5% by weight, of water based on the total weight of the liquid reaction medium. The reaction can in particular be carried out in an organic solvent.

Suitable organic solvents are for example aliphatic hydrocarbons, preferably having 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, tetrachloromethane, dichloroethane or tetrachloroethane, aromatic hydrocarbons such as benzene, toluene, the xylenes, chlorobenzene or dichlorobenzene, aliphatic acyclic and cyclic ethers or alcohols, preferably having 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof. The aforementioned ethers, especially tetrahydrofuran, are particularly preferably used.

The reduction with reductase can for example be carried out in an aqueous organic reaction medium such as, for example, water/isopropanol in any mixing ratio such as, for example, 1:99 to 99:1 or 10.90 to 90:10, or an aqueous reaction medium.

The substrate (1) is preferably employed in the enzymatic reduction in a concentration from 0.1 g/l to 500 g/l, particularly preferably from 1 g/l to 50 g/l, and can be fed in continuously or discontinuously.

The enzymatic reduction ordinarily takes place at a reaction temperature below the deactivation temperature of the reductase employed and above −10° C. It is particularly preferably in the range from 0 to 100° C., in particular from 15 to 60° C. and specifically from 20 to 40° C., e.g. at about 30° C.

A preferred embodiment of the process of the invention comprises performing the reaction in the presence of divalent metal ions, in particular in the presence of Ca, Mg, Mn, Zn, Ni, Fe, Mo ions. Advantageously, the concentration of the alkaline earth metal ions is chosen to be about the same as the concentration of the substrate to be used (alkene derivative of the general formula I). The addition of equimolar concentrations of divalent metal ions, with respect to the substrate, is recommended, in particular if said substrate, due to its structure, is capable of complexing metal ions, for example in the case of dicarboxylic acid derivatives.

A possible procedure for example is to mix the substrate (1) with the reductase, the solvent and, if appropriate, the coenzymes, if appropriate a second dehydrogenase to regenerate the coenzyme and/or further reducing agents, thoroughly, e.g. by stirring or shaking. However, it is also possible to immobilize the reductase in a reactor, for example in a column, and to pass a mixture comprising the substrate and, if appropriate, coenzymes and/or cosubstrates through the reactor. For this purpose it is possible to circulate the mixture through the reactor until the desired conversion is reached.

The reduction is ordinarily carried out until the conversion is at least 70%, particularly preferably at least 85% and in particular at least 95%, based on the substrate present in the mixture. The progress of the reaction, i.e. the sequential reduction of the double bond, can moreover be followed by conventional methods such as gas chromatography or high pressure liquid chromatography.

"Functional equivalents" or analogues of the specifically disclosed enzymes are in the context of the present invention polypeptides which differ therefrom and which still have the desired biological activity such as, for example, substrate specificity. Thus, "functional equivalents" mean for example enzymes which catalyze the model reaction and which have at least 20%, preferably 50%, particularly preferably 75%, very particularly preferably 90%, of the activity of an enzyme comprising one of the amino acid sequences listed under SEQ ID NO:1, 2 or 3. Functional equivalents are additionally preferably stable between pH 4 and 10 and advantageously have a pH optimum between pH 5 and 8 and a temperature optimum in the range from 20° C. to 80° C.

"Functional equivalents" also mean according to the invention in particular mutants which have an amino acid other than that specifically mentioned in at least one sequence position of the abovementioned amino acid sequences but nevertheless have one of the abovementioned biological activities. "Functional equivalents" thus comprise the mutants obtainable by one or more amino acid additions, substitutions, deletions and/or inversions, it being possible for said modifications to occur in any sequence position as long as they lead to a mutant having the property profile according to the invention. Functional equivalents also exist in particular when the reactivity patterns agree qualitatively between mutant and unmodified polypeptide, i.e. for example identical substrates are converted at a different rate.

Examples of suitable amino acid substitutions are to be found in the following table:

| Original residue | Substitution examples |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the described polypeptides and "functional derivatives".

"Precursors" are in this connection natural or synthetic precursors of the polypeptides with or without the desired biological activity.

"Functional derivatives" of polypeptides of the invention can likewise be prepared on functional amino acid side groups or on their N- or C-terminal end with the aid of known techniques. Such derivatives comprise for example aliphatic esters of carboxylic acid groups, amides of carboxylic acid groups, obtainable by reaction with ammonia or with a primary or secondary amine; N-acyl derivatives of free amino groups prepared by reaction with acyl groups; or O-acyl derivatives of free hydroxy groups prepared by reaction with acyl groups.

In the case where protein glycosylation is possible, "functional equivalents" of the invention comprise proteins of the type designated above in deglycosylated or glycosylated form, and modified forms obtainable by altering the glycosylation pattern.

"Functional equivalents" of course also comprise polypeptides which are obtainable from other organisms, and naturally occurring variants. For example, it is possible to establish ranges of homologous sequence regions by comparison of sequences, and to ascertain equivalent enzymes based on the specific requirements of the invention.

"Functional equivalents" likewise comprise fragments, preferably individual domains or sequence motifs, of the polypeptides of the invention, which have, for example, the desired biological function.

"Functional equivalents" are additionally fusion proteins which comprise one of the abovementioned polypeptide sequences or functional equivalents derived therefrom and at least one further, heterologous sequence which is functionally different therefrom and is in functional N- or C-terminal linkage (i.e. with negligible mutual functional impairment of the parts of the fusion protein). Nonlimiting examples of such heterologous sequences are, for example, signal peptides or enzymes.

Homologues of the proteins of the invention can be identified by screening combinatorial libraries of mutants, such as, for example, truncation mutants. For example, a variegated library of protein variants can be generated by combinatorial mutagenesis at the nucleic acid level, such as, for example, by enzymatic ligation of a mixture of synthetic oligonucleotides. There is a large number of methods which can be used to prepare libraries of potential homologues from a degenerate oligonucleotide sequence. Chemical synthesis of a degenerate gene sequence can be carried out in an automatic DNA synthesizer, and the synthetic gene can then be ligated into a suitable expression vector. Use of a degenerate set of genes makes it possible to provide all the sequences which encode the desired set of potential protein sequences in one mixture. Methods for synthesizing degenerate oligonucleotides are known to the skilled worker (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

Several techniques are known in the art for screening gene products of combinatorial libraries which have been prepared by point mutations or truncation, and for screening cDNA libraries for gene products having a selected property. These techniques can be adapted to the rapid screening of gene libraries which have been generated by combinatorial mutagenesis of homologues of the invention. The most commonly used techniques for screening large gene libraries, which are subject to high-throughput analysis, include the cloning of the gene library into replicable expression vectors, transformation of suitable cells with the resulting vector library and expression of the combinatorial genes under conditions under which detection of the desired activity facilitates isolation of the vector which encodes the gene whose product has been detected. Recursive ensemble mutagenesis (REM), a technique which increases the frequency of functional mutants in the libraries, can be used in combination with the screening tests to identify homologues (Arkin and Yourvan (1992) PNAS 89:7811-7815; Delgrave et al. (1993) Protein Engineering 6(3):327-331).

The invention further relates to nucleic acid sequences (single- and double-stranded DNA and RNA sequences such as, for example, cDNA and mRNA) which code for an enzyme having reductase activity according to the invention. Nucleic acid sequences which code for example for amino acid sequences shown in SEQ ID NO:1, 2 or 3 characteristic partial sequences thereof are preferred.

All nucleic acid sequences mentioned herein can be prepared in a manner known per se by chemical synthesis from the nucleotide building blocks, such as, for example, by fragment condensation of individual overlapping complementary nucleic acid building blocks of the double helix. Chemical synthesis of oligonucleotides can take place for example in a known manner by the phosphoamidite method (Voet, Voet, 2nd edition, Wiley Press New York, pages 896-897). Addition of synthetic oligonucleotides and filling in of gaps using the Klenow fragment of DNA polymerase and ligation reactions, and general cloning methods are described in Sambrook et al. (1989), Molecular Cloning: A laboratory manual, Cold Spring Harbor Laboratory Press.

Further embodiments for carrying out the enzymatic reduction process of the invention:

The pH in the process of the invention is advantageously kept between pH 4 and 12, preferably between pH 4.5 and 9, particularly preferably between pH 5 and 8.
min. 98% ee reached.

It is possible to use for the process of the invention growing cells which comprise nucleic acids, nucleic acid constructs or vectors coding for the reductase. It is also possible to use resting or disrupted cells. Disrupted cells mean for example cells which have been made permeable by a treatment with, for example, solvents, or cells which have been disintegrated by an enzyme treatment, by mechanical treatment (e.g. French press or ultrasound) or by any other method. The crude extracts obtained in this way are advantageously suitable for the process of the invention. Purified or partially purified enzymes can also be used for the process. Immobilized microorganisms or enzymes are likewise suitable and can advantageously be used in the reaction.

The process of the invention can be carried out batchwise, semi-batchwise or continuously.

The process can advantageously be carried out in bioreactors as described for example in Biotechnology, Vol. 3, 2nd edition, Rehm et al. editors (1993), especially chapter II.

The products prepared in the process of the invention may be isolated from the reaction medium by methods familiar to the skilled worker and may be purified, if desired. These methods include distillation methods, chromatographic methods, extraction methods and crystallization methods. Depending on the requirement, purification of the products may be enhanced considerably by combining a plurality of said methods.

The following examples are intended to illustrate the invention without, however, restricting it. Reference is made to the appended figures in this connection, which show:
Experimental Section
General Protocol of Asymmetric Bioreduction Asymmetric bioreduction of the substrates was carried out according to the following general protocol using the isolated enzymes YqjM, OPR1, OPR3. Due to poor solubility in water, N-phenyl-2-methylmaleimide was added as a 10% solution in DMF (final concentration 1%).

The enzyme preparation (100-200 µg) was added to a solution of the substrate (5 mM) in Tris buffer, 50 mM pH 1.5 (0.8 ml) with NADH or NADPH cofactor (15 mM), and the reaction was carried out at 30° C. with shaking (140 rpm). After 48 hours, the reaction mixture was extracted with ethyl acetate and the reaction products were analyzed by GC.

The following procedure was chosen when using the cofactor recycling system:
NADH/FDH System A mixture of substrate (5 mM), oxidized cofactor $NAD^+$ (100 µM), ammonium formate (20 mM) in 50 mM Tris buffer pH 7.5 (0.8 ml) was admixed with FDH (10 u), after the enzyme (100-200 µg) had been added, and the reaction was carried out at 30° C. (140 rpm) for 48 hours.
NADH/GDH A mixture of substrate (5 mM), oxidized cofactor $NAD^+$ (100 µM), glucose (20 mM) in 50 mM Tris buffer pH 7.5 (0.8 ml) was admixed with (D)-GDH (10 u), after the enzyme (100-200 µg) had been added, and the reaction was carried out at 30° C. (140 rpm) for 48 hours.
NADPH/G6PDH A mixture of substrate (5 mM), oxidized cofactor $NADP^+$ (10 µM), glucose 6-phosphate (20 mM) in 50 mM Tris buffer pH 7.5 (0.8 ml) was admixed with G6PDH (10 u), after the enzyme (100-200 µg) had been added, and the reaction was carried out at 30° C. (140 rpm) for 48 hours.

GC-FID analyses were carried out in a Varian 3800 gas chromatograph with $H_2$ as carrier gas (14.5 psi).
1-Nitro-2-phenylpropene:

Determination of conversion: the products obtained were analyzed by GC-FID using a 6% cyanopropylphenylpolysiloxane phase capillary column (Varian CP-1301, 30 m, 0.25 mm, 0.25 µm film) with a split ratio of 30:1. Program: 120° C./min to 180° C., 20° C./min to 220° C., 2 min hold. Retention times were as follows: limonene (internal standard) 3.81 min, 1-nitro-2-phenylpropane 8.87 min, 1-nitro-2-phenylpropene Z/E 9.55 10.27 min resp. Determination of enantiomeric excess and absolute configuration: enantiomeric excess was determined using a cyclodextrin-bound dimethylpolysiloxane phase capillary column (CP-Chirasil-DEX CB, 25 μm, 0.32 mm, 0.25 μm film) with a split ratio of 25:1. Temperature program: 105° C. 5 min. hold, 1° C./min to 120° C., 6 min. hold, 20° C./min to 180° C., 2 min. hold. Retention times were as follows: (S)- and (R)-1-nitro-2-phenylpropane 12.06 and 12.57 min, resp. The absolute configuration of 1-nitro-2-phenylpropane was determined by coinjecting an independently synthesized reference sample (J. Org. Chem. 1989, 54, 1802-1804)

Citral

Determination of conversion: the products obtained were analyzed by GC-FID using a polyethylene glycol phase capillary column (Varian CP-Wax 52CB, 30 m, 0.25 mm, 0.25 μm film) with a split ratio of 20:1. Program: 100° C. hold for 2 min. 15° C./min to 240° C., 10 min. hold. Retention times were as follows: citronellal 5.21 min, 1-octanol (internal standard) 5.83 min, geranial 7.53 min.

Determination of enantiomeric excess and absolute configuration: the enantiomeric excess of citronellal was determined using a modified β-cyclodextrin capillary column (hydrodex-β-TBDAc, 25 m, 0.25 mm) temperature program: 40° C. hold 2 min, 4° C./min to 120° C., 1 min. hold, 20° C./min to 180° C., 3 min. hold. Retention times were as follows: (S)- and (R)-citronellal 19.84 and 19.97 min resp. The absolute configuration of citronellal was determined by coinjecting a commercially available reference sample with known absolute configuration.

N-Phenyl-2-methylmaleimide

Determination of conversion: the products obtained were analyzed by GC-FID using a 6% cyanopropylphenylpolysiloxane phase capillary column (Varian CP-1301, 30 m, 0.25 mm, 0.25 μm film) with a split ratio of 30:1. Program: 110° C. hold 2 min, 30° C./min to 210° C., 6 min. hold. Retention times were as follows: limonene (internal standard) 3.69 min, N-phenyl-2-methylmaleimide 8.77 min, N-phenyl-2-methylsuccinimide 9.89 min.

Determination of the enantiomeric excess and absolute configuration: enantiomeric excess was determined on a Shimadzu chiral HPLC using a Chiralcel OD-H column and a solution of n-heptane/ethanol 95:5 as eluent. 80 μl were eluted isocratically at 18° C. over 33 min. Retention times were as follows: (S)- and (R)-N-phenyl-2-methylsuccinimide 27.0 and 29.1 min resp. The absolute configuration of 1-N-phenyl-2-methylsuccinimide was determined by CD spectroscopy (J. Mol. Catal. B:Enzym 2005, 32, 131-134).

Cyclic Enones:

Determination of conversion: the products obtained were analyzed by GC-FID using a 6% cyanopropylphenylpolysiloxane phase capillary column (Varian CP-1301, 30 m, 0.25 mm, 0.25 μm film) with a split ratio of 30:1. Program: 80° C. hold for 10 min, 30° C./min to 200° C., 3 min. hold. Retention times were as follows: 2-methyl cyclopentanone 4.27 min, 3-methyl cyclopentanone 4.44 min, 2-methyl 2-cyclopenten-1-one 5.82 min, 3-methyl cyclohexanone 7.27 min, (R)-limonene (internal standard) 8.59 min, 3-methyl 2-cyclopenten-1-one 8.77 min, 3-methyl 2-cyclohexen-1-one 11.77 min. resp.

Determination of enantiomeric excess and absolute configuration: enantiomeric excess was determined using a modified R-cyclodextrine capillary column (Chiraldex B-TA, 40 m, 0.25 mm) with a split ratio of 25:1. Temperature program: 80° C. 17 min hold, 30° C./min to 180° C., 2 min. hold. Retention times were as follows: (S)- and (R)-3-methyl cyclopentanone 8.08 and 8.29 min, (R)- and (S)-2-methyl cyclopentanone 6.55 and 6.77 min, (R)- and (S)-3-methyl cyclohexanone 13.96 and 15.09 min. The absolute configuration of 3-methyl cyclopentanone and 3-methyl cyclohexanone were determined by coinjecting a commercially available reference sample with known absolute configuration. The absolute configuration of 2-methyl cyclopentanone was determined by coinjecting an independently synthesized reference sample with known absolute configuration (Tetrahedron: Asymmetry 2001, 12, 1479-1483).

What is claimed is:

1. A process for enzymatically preparing a compound of formula (2) from an unsaturated alkene derivative of formula (I)

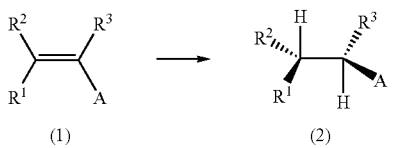

wherein

A is a nitro radical (—$NO_2$), a ketone radical (—CRO), an aldehyde radical (—CHO), or a carboxyl radical (—COOR), wherein R is H or an optionally substituted $C_1$-$C_6$-alkyl radical;

$R^1$, $R^2$ and $R^3$ are, independent of one another, H, $C_1$-$C_6$-alkyl, $C_2$-$C_6$-alkenyl, carboxyl, or a carbo- or heterocyclic, aromatic or nonaromatic radical, wherein said carbo- or heterocyclic, aromatic or nonaromatic radical is optionally substituted, or $R^1$ is linked to $R^3$ so as to become part of a 4-8-membered cycle, or $R^1$ is linked to R so as to become part of a 4-8-membered cycle, with the proviso that $R^1$, $R^2$, and $R^3$ may not be identical;

comprising reducing a compound of formula (1) with a reductase comprising:
(i) a polypeptide selected from the group consisting of SEQ ID NOs: 1, 2, and 3; or
(ii) a functionally equivalent polypeptide having at least 95% sequence identity to a polypeptide selected from the group consisting of SEQ ID NOs: 1, 2, and 3.

2. The process of claim 1, wherein said reduction is carried out using NADPH or NADH as cofactor.

3. The process of claim 2, wherein the cofactor used is regenerated enzymatically.

4. The process of claim 3, wherein the cofactor is regenerated by glucose dehydrogenase or formate dehydrogenase or a secondary alcohol.

5. The process of claim 1, wherein the reduction is carried out in an aqueous, aqueous-alcoholic, or alcoholic reaction medium.

6. The process of claim 1, wherein the reductase has been immobilized.

7. The process of claim 1, wherein the reductase is obtained from *Bacillus subtilis* or *Lycopersicum esculentum*.

8. The process of claim 1, wherein $R^1$ is methyl and A is a ketone radical.

9. The process of claim 1, wherein the reduction is carried out at a temperature in the range from 0 to 45° C. and/or at a pH in the range of from 6 to 8.

10. The process of claim 1, wherein the reduction is performed in the presence of divalent metal ions.

* * * * *